(12) United States Patent
Popov (10) Patent No.: US 8,298,186 B2
(45) Date of Patent: Oct. 30, 2012

(54) CATHETER INTRODUCER

(76) Inventor: Sergey Popov, Sheva (IL)

( * ) Notice: Subject to any disclaimer, the term of this patent is extended or adjusted under 35 U.S.C. 154(b) by 846 days.

(21) Appl. No.: 10/579,534

(22) PCT Filed: Nov. 11, 2004

(86) PCT No.: PCT/IL2004/001036
§ 371 (c)(1),
(2), (4) Date: Apr. 18, 2007

(87) PCT Pub. No.: WO2005/046750
PCT Pub. Date: May 26, 2005

(65) Prior Publication Data
US 2007/0260185 A1    Nov. 8, 2007

(30) Foreign Application Priority Data
Nov. 16, 2003  (IL) .......................................... 158888

(51) Int. Cl.
*A61M 5/178*   (2006.01)
*A61M 25/00*   (2006.01)
*A61M 31/00*   (2006.01)

(52) U.S. Cl. ..................... 604/164.08; 604/263; 604/500

(58) Field of Classification Search .................. 604/263, 604/164.08
See application file for complete search history.

(56) References Cited

U.S. PATENT DOCUMENTS

| | | | |
|---|---|---|---|
| 5,098,410 A * | 3/1992 | Kerby et al. | 604/256 |
| 5,352,205 A * | 10/1994 | Dales et al. | 604/158 |
| 5,755,709 A * | 5/1998 | Cuppy | 604/164.12 |
| 5,795,339 A * | 8/1998 | Erskine | 604/264 |
| 5,879,334 A * | 3/1999 | Brimhall | 604/165.04 |
| 5,997,507 A | 12/1999 | Dysarz | |
| 6,942,652 B1 | 9/2005 | Pressly, Sr. et al. | |
| 6,972,002 B2 * | 12/2005 | Thorne | 604/164.08 |
| 2002/0055716 A1* | 5/2002 | Nakagami | 604/164.12 |
| 2004/0181192 A1* | 9/2004 | Cuppy | 604/256 |

FOREIGN PATENT DOCUMENTS

EP   0567321 A2   10/1993
GB   2060399 D2   5/1981

* cited by examiner

*Primary Examiner* — Nicholas Lucchesi
*Assistant Examiner* — Ian Holloway
(74) *Attorney, Agent, or Firm* — Daniel J. Swirsky; AlphaPatent Associates Ltd.

(57) ABSTRACT

Safety catheter introducer 135 (see FIG. 13) comprises catheter 131, needle 136, a safety means including needle protector 138 and actuated by trigger 149, as well as catheter cap 150. The latter is initially detachably retained on hexagonal shank 153 of protector 138 by moderate friction forces, and male luer member 145 is protected from contact with personnel by cap lateral wall 147. After the catheter emplacement, needle withdrawal and needle sharp point protection, operator turns protector 138 through 180 degrees and fixes cap 150 on catheter 131 by thread 152 using protector 138 as a cap holder. In doing so, male luer member 145 occludes the catheter entrance. Thereafter, operator easily detaches the protector from the cap. As a result, catheter 131 remains in patient's vein being closed with cap 150.

8 Claims, 9 Drawing Sheets

CATHETER INTRODUCER

This application is a U.S. National Phase Application under 35 U.S.C. 371 of PCT International Application No. PCT/IL2004/001036, which has an international filing date of Nov. 11, 2004, and which claims priority from Israel Patent Application No. 158,888, filed Nov. 16, 2003, and incorporated herein by reference in its entirety.

BACKGROUND

1. Field of the Invention

The invention generally relates to the catheter introducers for intravascular catheterization and more particularly to the catheter insertion apparatus for blood vessel catheterization with a needle tip protective system.

2. Prior Art of the Invention

The catheter introducer for intravascular catheterization includes, as a rule, a catheter having a catheter hub and an axial through channel with a proximal end portion made as a female luer lock portion, a needle assembly comprising a needle with a distal sharp point extending through the catheter axial through channel, and a safety means having a protector for protecting the needle distal sharp point after introducing the catheter into a blood vessel and needle withdrawal from the catheter. In the operation position, the needle is housed inside the catheter through axial channel and the needle distal sharp point protrudes distally from the catheter, allowing the operator the introduction of the catheter into patient's vein. After catheter emplacement, operator withdraws the needle from the catheter unit and closes the catheter hub with a catheter cap, which initially is located separately from the needle assembly. In doing so, the male tapered luer member of the catheter cap occludes the female luer lock portion of the catheter, thereby preventing the catheter from blood leakage and infecting from outside. To close the catheter hub by the catheter cap, operator must release the hand from the withdrawn needle assembly, find the catheter cap, take it with a hand so that its male tapered luer member is faced outwardly, and set it onto the catheter hub. The disadvantage of these operations is that they are inconvenient, take certain time and operator's attention, and do not exclude the infection of the catheter cap. Several attempts to eliminate these disadvantages are known. Specifically, U.S. Pat. Nos. 4,496,348, 4,874,377 and 5,041,097 are disclosed the catheter placement devices with the resilient self-sealing member in the catheter hub, intended for automatic closing the catheter hub after withdrawing the needle. These designs did not find the application because of its high cost and low reliability.

Another disadvantages of known catheter introducers with safety means for protecting the needle distal sharp point can be considered using patent U.S. Pat. No. 4,747,831 as example. This patent discloses a cannula insertion needle set with safety retracting needle, which includes a needle unit having a needle with a distal sharp point and a needle hub, a hollow handle in the form of a barrel for containing a needle unit and protecting the needle distal sharp point in the needle protection position, and a safety means including a latch, a trigger, and a retracting spring disposed inside the barrel. After inserting the cannula (catheter) into patient's vein, operator displaces the latch by means of squeezing or rotating the trigger, thereby releasing the retracting spring, which retracts the needle unit into the protection position inside the barrel. The disadvantage of this cannula insertion set is the complexity of its safety mechanism, wherein the trigger-latch and the barrel are made as separate parts. As a result, the cost of manufacturing and assembling the set is increased. Another disadvantages are the location of the trigger in the zone of the active manipulations of operator's fingers during the cannula emplacement and the direction of the movement needed for the trigger activation. This is inconvenient in operation and decreases the operation reliability creating the danger of inadvertent trigger activation and, as a result, premature retraction of the needle unit into the protection position. The disadvantage is also the considerable impact of the needle hub and the stop member at the end of the needle unit retraction.

SUMMARY

The objective of the present invention is reducing the time needed for closing the catheter hub after needle withdrawal.

Another objective is improving the convenience of personnel operations.

Another objective is improving the sanitation during the process of catheter emplacement.

Another objective is restricting the probability of the blood leakage through the catheter after needle withdrawal.

Another objective is the simplification of the catheter introducer design and assembly and, as a result, decreasing its cost with simultaneous improving its performance.

Another objective is heightening the operation reliability of the catheter introducer.

Another objective is providing the adaptability of the catheter introducer to the various designs of the catheter and catheter cap.

Another objective is reducing the price of the shipping package of the catheter introducer.

Another objective is providing the wide scope of catheter introducer application.

The above noted objectives of the present invention are accomplished with a catheter introducer, including: a catheter having a catheter hub and an axial through channel with a proximal end portion made as a female luer lock portion; a needle assembly comprising a needle with a distal sharp point which extends through the catheter channel, and a safety means having a protector for protecting the needle distal sharp point after introducing the catheter into a blood vessel; and a catheter cap for occluding a proximal opening of the catheter after the transfer of the needle to a protected position, therewith the catheter cap is detachably positioned on the needle assembly so that, after the needle protection, the catheter cap is accessible for occluding the catheter proximal opening without previous detachment of the catheter cap from the needle assembly. After the catheter emplacement, the needle withdrawal, and the needle sharp point protection, operator closes the catheter with the catheter cap using the needle assembly as a holder of the catheter cap. In doing so, there is no need to release the hand from the withdrawn needle assembly, to find the catheter cap, to take it with a hand and to properly direct it. As a result, the operation time is reduced and the operation convenience is improved. The possibility of the catheter closure immediately after the needle withdrawal allows the practical elimination of the blood leakage from the catheter hub and infecting the catheter hub interior. The mounting elements of the needle assembly for mounting the catheter cap on the needle assembly are made as an integral parts of the needle assembly housing and practically do not increase the needle assembly cost. Moreover, the mounting elements easily can be adapted to any design of the catheter cap, thereby widening the scope of catheter introducer application. In version embodiment of the catheter introducer, a needle hub is movable in a guide so that, in a duty ready position, the proximal end of the needle hub is distally of the proximal end of the guide and the catheter cap is positioned at the guide proximal end, and, in the needle retracted position, the needle hub proximal end is proximally of the guide proximal end and the catheter cap is positioned at the needle hub proximal end as a result of disengaging the catheter cap from the guide and engaging it with the needle hub during the transition of the needle hub from the duty ready position into the needle protected position. This version allows additional widening the scope of the present catheter introducer application.

In version embodiment, the catheter cap and the detail of the need assembly on which it is positioned are made as a single part, so that the catheter cap is connected to the needle assembly with a fragile link to be easy broken after mounting the catheter cap onto the catheter. This allows simplifying the design and reducing the cost of the catheter introducer.

In version embodiment, the catheter introducer is provided with a shielding means preventing the catheter cap interior from accidental contact with operator's hands, thereby improving the operation sanitation. Besides, this mode of the catheter closure does not need for any changes of the catheter design.

The protector of the safety means of the present invention: is made in the form of a barrel containing the needle in the needle protection position; has a springy retracting element; has a stop member located at a proximal end of the barrel and made in the form of a flexible ribbon which also fulfils a role of an impact damper; is provided with a latch controlled by a manual trigger. The barrel, latch and trigger are made as a single part including a flexible link, which connects the trigger-latch and barrel and provides the mobility of the trigger-latch relative to the barrel. This decreases the cost of the catheter introducer fabrication. The latch protrudes inside of the barrel and has sloping proximal surface, which along with the flexible link simplifies putting together the barrel and a needle unit. The trigger design allows it arrangement somewhat proximally of the zone of the operator's finger manipulations. This improves the operation convenience and reliability of the catheter introducer. The proximally directed movement needed for the trigger activation is not inherent in operator's natural motions. This additionally heightens the reliability of the catheter introducer operation, eliminating the inadvertent trigger activation. Moreover, this simplifies and makes cheaper the needed shipping package of the catheter introducer, permitting the use of a soft package, as the trigger cannot be activated by simple external press. In turn, the soft shipping package obviates the restriction for using the catheter introducer with the catheters having a side port and side wings. As a result, the scope of catheter introducer application widens. The presence of the impact damper additionally improves the ergonomic properties of the catheter introducer, therewith making the impact damper and stop member as a single part allows avoiding the increase of the catheter introducer cost.

BRIEF DESCRIPTION OF THE DRAWINGS

FIGS. 1 to 6 show the version of the catheter introducer with needle retracting springy safety means, wherein the catheter cap is made without a thread, positioned laterally at the distal end of the needle assembly, and its tapered male luer member is directed distally.

FIGS. 7 to 12 illustrate the process of the mounting of the catheter cap.

FIGS. 13 to 18 show the version of the catheter introducer with needle retracting springy safety means, wherein the catheter cap, shown in its longitudinal section, is made with a thread, initially positioned on the proximal face of the needle assembly with the tapered male luer member directed proximally, as well as the process of the catheter cap mounting onto the catheter.

FIGS. 19 to 25 show the version of the catheter introducer with needle retracting springy safety means and impact damper, wherein the catheter cap is made without a thread, initially positioned on the top of the needle assembly distal end, and its tapered male luer member is directed distally.

FIGS. 26 to 29 show the version of the catheter introducer with needle retracting springy safety means and impact damper in the form of flexible ribbon, without a catheter cap.

FIGS. 30 to 34 show the version of the catheter introducer with needle retracting springy safety means and the impact damper in the form of the inclined friction member, without a catheter cap.

FIGS. 35 to 40 show the version of the catheter introducer with manually driven needle retracting safety means, wherein the catheter cap is transposed from the needle hub guide to the needle hub during the needle transition from the duty ready position into the protected position.

DETAILED DESCRIPTION OF THE INVENTION

A description of the present invention is offered with reference made to the attached drawings.

Figure 1:
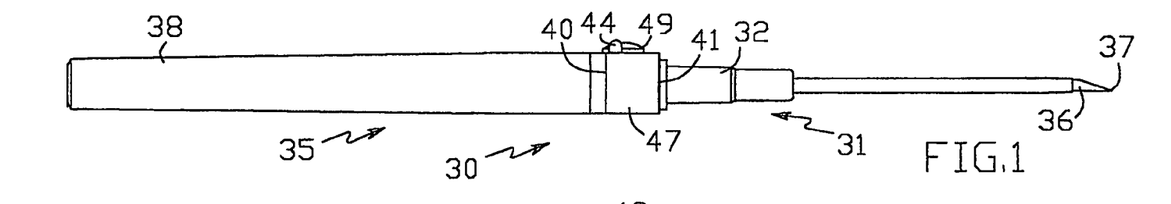
FIG. 1 shows the general side view of the catheter introducer.
Figure 2:
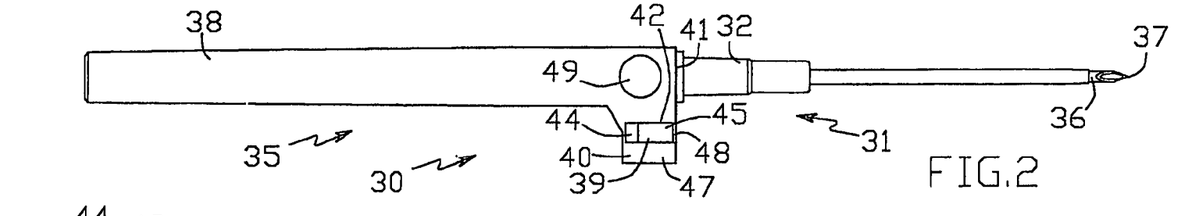
FIG. 2 shows the general top view of the catheter introducer.
Figures 3, 5, 6:
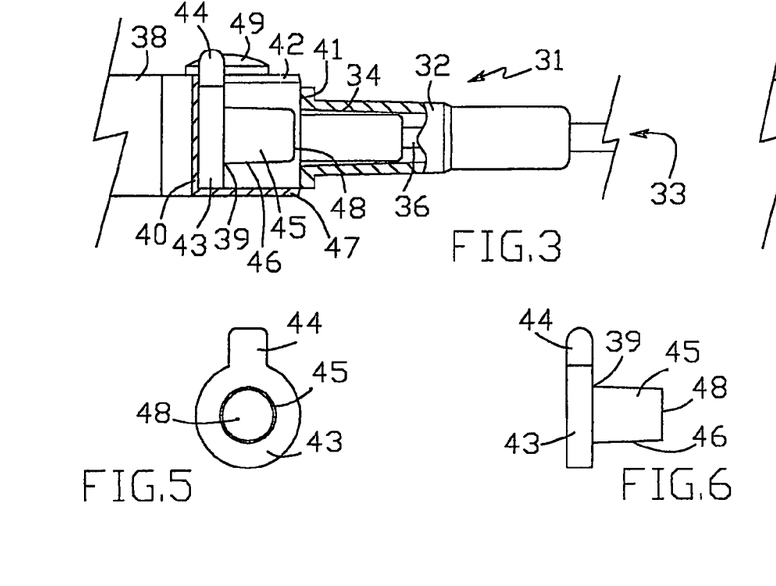
FIG. 3 shows the close-up, partial, side view of the catheter introducer with partial section.
FIGS. 5, 6 show the front and side views of the catheter cap, respectively.
Figure 4:
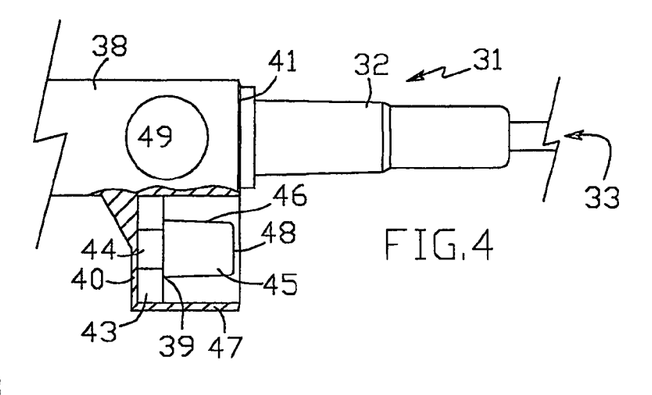
FIG. 4 shows the close-up, partial, top view of the catheter introducer with partial section.
Figure 7:
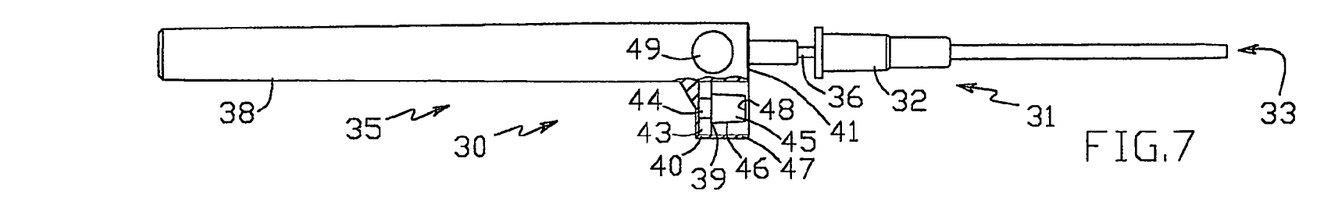
FIG. 7 shows the needle withdrawal from the catheter after catheter emplacement.
Figure 8:
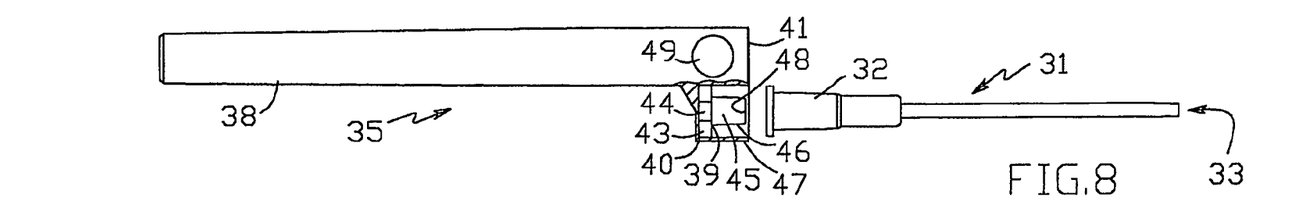
FIG. 8 shows the catheter cap position immediately before mounting the catheter cap onto the catheter.
Figure 9:
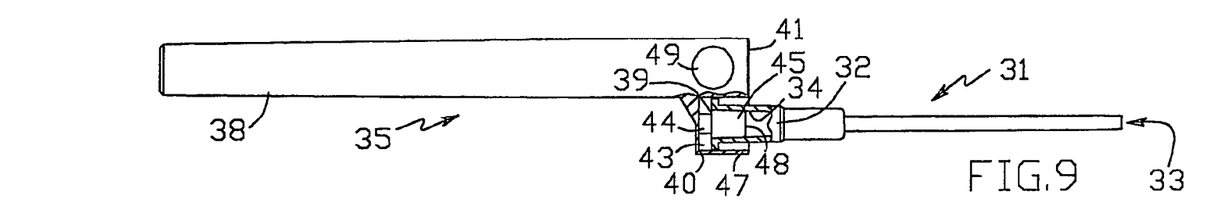
FIG. 9 shows introducing the tapered male luer member of the catheter cap into the female luer lock portion of the catheter.
Figure 10:
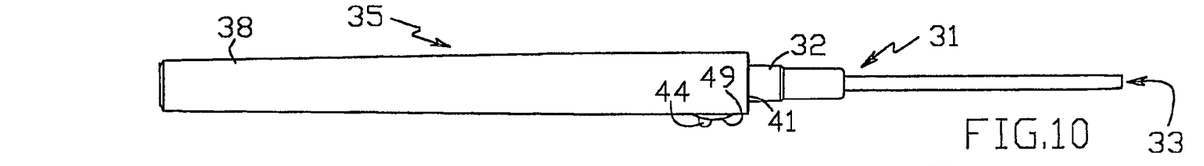
FIG. 10 shows the final stage of the catheter cap mounting onto the catheter, after which the needle assembly has to be detached from the catheter cap.
Figure 11:
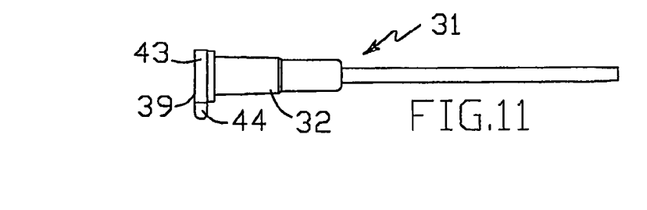
FIGS. 11, 12 show the catheter closed with the catheter cap.
Figure 12:
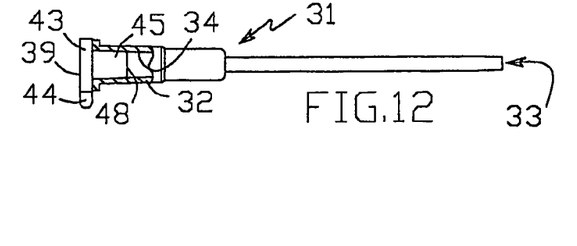
Figure 13:
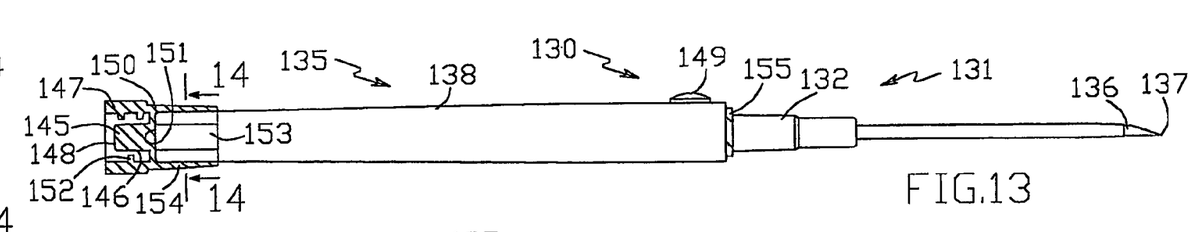
FIG. 13 shows the general side view of the catheter introducer before the catheter emplacement.
Figure 14:
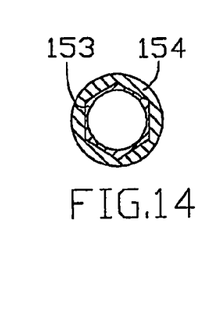
FIG. 14 shows the close-up cross section of the catheter introducer in the zone of the catheter cap disposition.

The catheter introducer 30 shown in FIGS. 1 to 12 includes: catheter 31 having catheter hub 32 and axial through channel 33 with proximal end portion made as a female luer lock portion 34; needle assembly 35 comprising needle 36 with distal sharp point 37 extending through catheter channel 33, and safety means having protector 38 for protecting needle distal sharp point 37 after introducing catheter 31 into a blood vessel; catheter cap 39 for occluding a proximal opening of catheter 31 after the transfer of the needle 36 to the protection position. Catheter cap 39 is detachably positioned on needle assembly 35 so that, after needle 36 protection, catheter cap 39 is accessible for occluding the catheter proximal opening without previous detachment of catheter cap 39 from needle assembly 35. The mounting means for mounting catheter cap 39 on needle assembly 35 includes first mounting element in the form of a receptacle 40 disposed at the site of needle assembly 35, which is distal end 41 of needle assembly 35 after retracting needle 36 into its protection position (see FIG. 8). Receptacle 40 is provided with a slot 42 and made as a single part with protector 38, thereby minimizing the increase of needle assembly 35. Second mounting element is located on catheter cap 39 and made in the form of back 43 provided with projection 44. Slot 42 and projection 44 are the stabilizing means designed to prevent the rotation of catheter cap 39 relative to needle assembly 35 during mounting catheter cap 39 onto catheter 31. In the initial position, back 43 of catheter cap 39 is housed inside receptacle 40 so that projection 44 enters slot 42 ruling out the rotation of catheter cap 39 relative to needle assembly 35. Some friction between the interior of receptacle 40 and lateral surfaces of back 43 prevents catheter cap 39 from spontaneous coming out receptacle 40 but does not prevent from coming out it under distally directed light axial effort. Catheter cap 39 has also tapered male luer member 45 directed distally and its lateral surface 46 is a sealing surface, which is intended to occlude the proximal opening of catheter 31 as a result of contact with the interior of female luer lock portion 34. External wall 47 of receptacle 40 encloses the open distal edge 48 of catheter cap 39 and somewhat protrudes distally beyond edge 48 thereby fulfilling the role of the shielding means preventing sealing surface 46 of catheter cap 39 from accidental contact with personnel before mounting catheter cap 39 onto catheter 31. This improves the operation sanitation of catheter introducer 30. After the catheter emplacement, operator draws trigger 49 in proximal direction, thereby activating the safety means of catheter introducer 30, and the spring of the safety means (not shown) transfers needle 36 into protector 38 separating catheter 31 and needle assembly 35. Then, operator sets catheter cap 39 coaxially with catheter 31 (FIG. 8) using protector 38 as a holder, introduces tapered male luer member 45 into female luer lock portion 34 of catheter 31 (FIG. 9) and somewhat rotates member 45 in portion 34 to increase their engagement when needed (FIG. 10). As a result, catheter cap 39 is reliably retained in catheter 31 by the coupling forces of two conical elements 45 and 34. Thereafter, operator disconnects needle assembly 35 from catheter cap 39 and catheter 31 remains in patients vein being closed with catheter cap 39 (FIGS. 11, 12). In doing so, there is no need to change the operator's hand position on protector 38, to find the catheter cap 39, to take it with a hand and to properly direct it As a result, the operation time is reduced and the operation convenience is improved. The possibility of the catheter closure immediately after the withdrawal of needle 36 allows the practical elimination of the blood leakage from the catheter hub and infecting the catheter hub interior.

Figure 15:
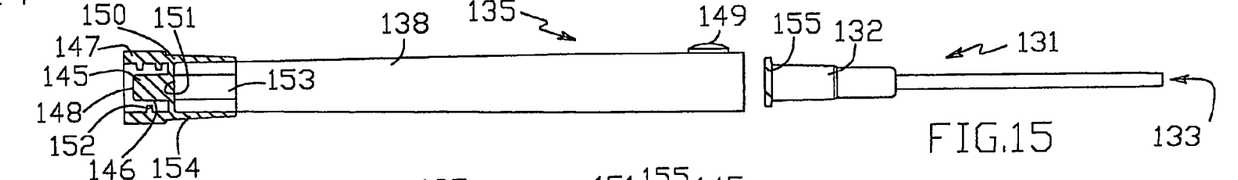
FIG. 15 shows the general side view of the catheter introducer after the catheter emplacement and needle retraction into the protection position.
Figures 16, 17:
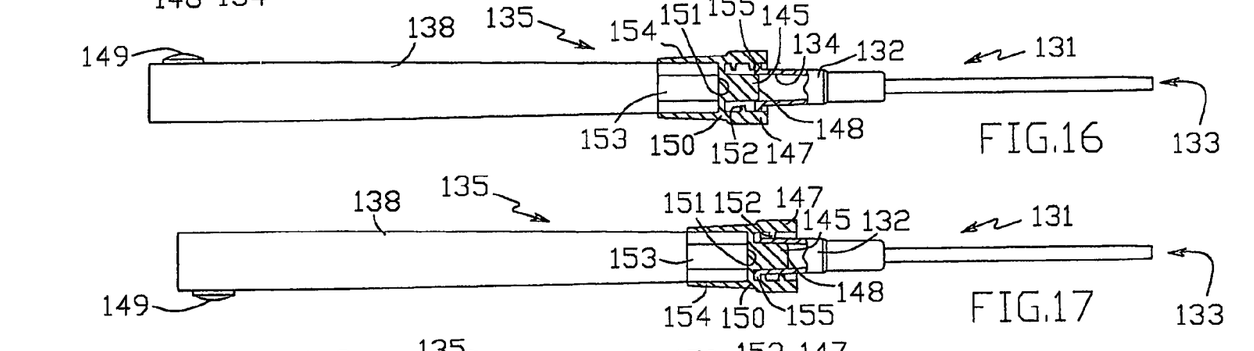
FIG. 16 shows the initial stage of the catheter cap mounting onto the catheter.
FIG. 17 shows the final stage of the catheter cap mounting onto the catheter, after which the needle assembly has to be detached from the catheter cap.
Figure 18:
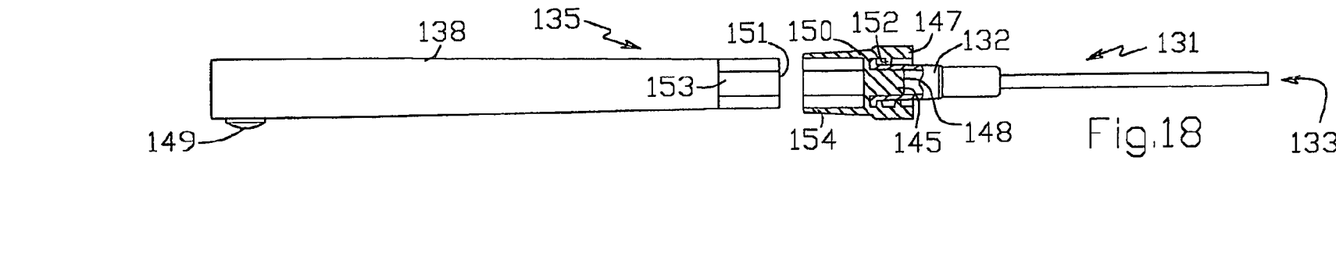
FIG. 18 shows the needle assembly and the catheter separated from one another after closing the catheter with the catheter cap.
Figure 19:
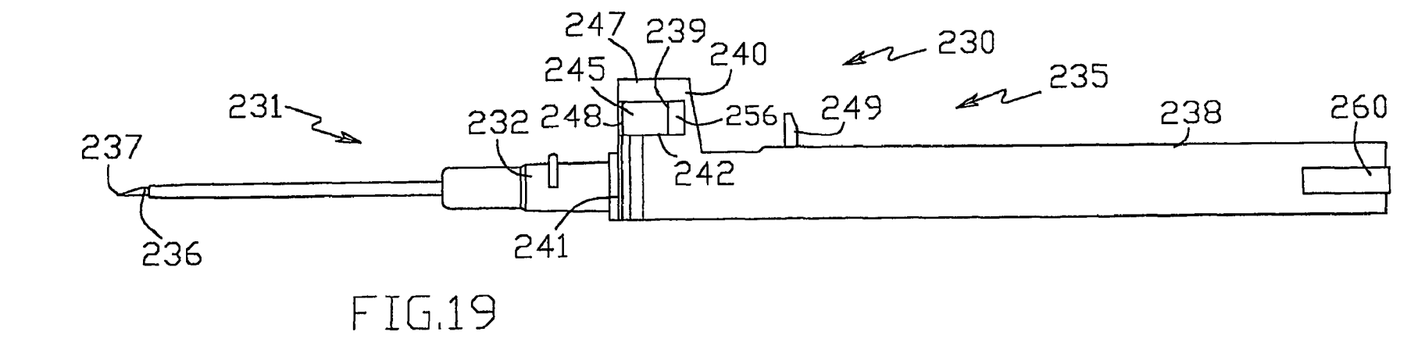
FIG. 19 shows the general side view of the catheter introducer before the catheter emplacement.
Figure 20:
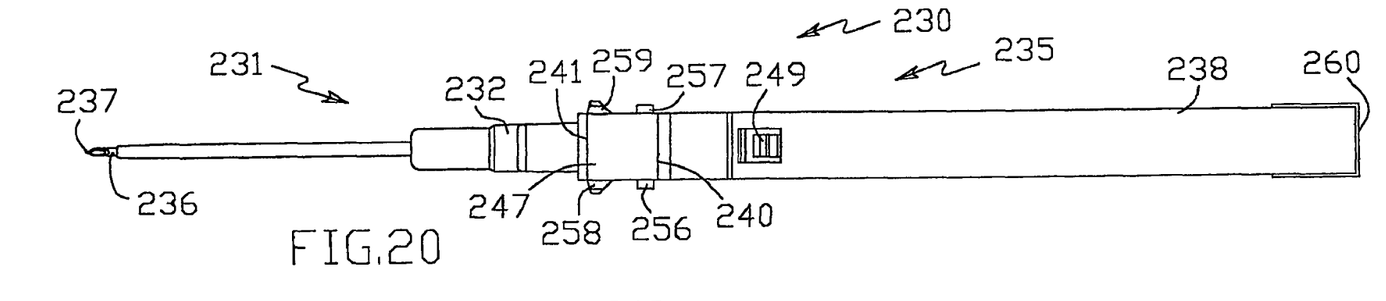
FIG. 20 shows the general top view of the catheter introducer before the catheter emplacement.
Figure 21:
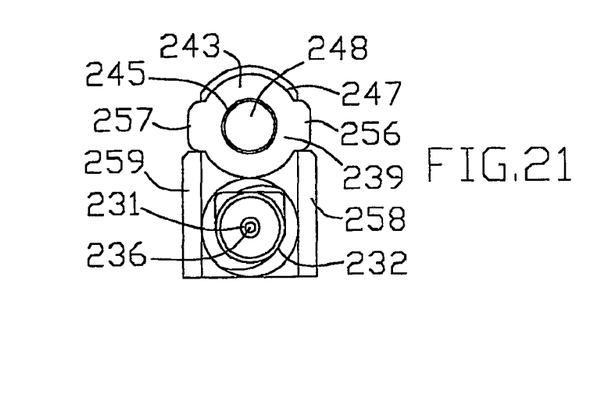
FIG. 21 shows the close-up front view of the catheter introducer before the catheter emplacement.

In version embodiment, catheter introducer 130 (FIGS. 13 to 18) is provided with catheter cap150 positioned at proximal end 151 of protector 138 of needle assembly 135. Catheter cap 150 is provided with thread 152 for fixing the catheter cap on catheter 131 and has tapered male luer member 145 initially directed proximally. The mounting means for mounting catheter cap 150 onto needle assembly 135 includes first mounting element in the form of proximal hexagonal shank 153 of protector 138 and second mounting element in the form of socket 154 of a hexagonal cross section. The hexagonal form of mounting elements 153 and 154 imparts them the properties of the stabilizing means preventing catheter cap 150 from the rotation relative to needle assembly 135 during mounting catheter cap 150 onto catheter 131. External wall 147 of catheter cap 150 encloses the open distal edge 148 of tapered male luer member 145 and somewhat protrudes distally beyond edge 148 thereby fulfilling the role of the shielding means preventing sealing surface 146 of catheter cap 150 from accidental contact with personnel before mounting catheter cap 150 onto catheter 131. This improves the operation sanitation of the catheter introducer. After the catheter emplacement, operator actuates trigger 149, thereby actuating the safety means of the catheter introducer. As a result, the spring of the safety means (not shown) transfers needle 136 into protector 138 separating catheter 131 and needle assembly 135 (see FIG. 15). Then, operator turns needle assembly 135 through 180° to set catheter cap 150 coaxially with catheter 131 in proximity to catheter hub 132 and, using protector 138 as a holder, screws catheter cap 150 onto threaded end 155 of catheter hub 132 (FIGS. 16, 17). Thereafter, operator disconnects needle assembly 135 from catheter cap 150 and catheter 131 remains in patients vein being closed with catheter cap 150 (FIGS. 18). This version embodiment provides the advantages identical to that for the previous version.

In another version embodiment (not shown), the catheter cap is provided with a thread for fixing the catheter cap on the catheter and has the tapered male luer member for sealing the catheter proximal opening, therewith the thread is made inside the external wall of the catheter cap, which is rotatable relative to the tapered male luer member to facilitate the fixation of the catheter cap on the catheter.

Figure 22:
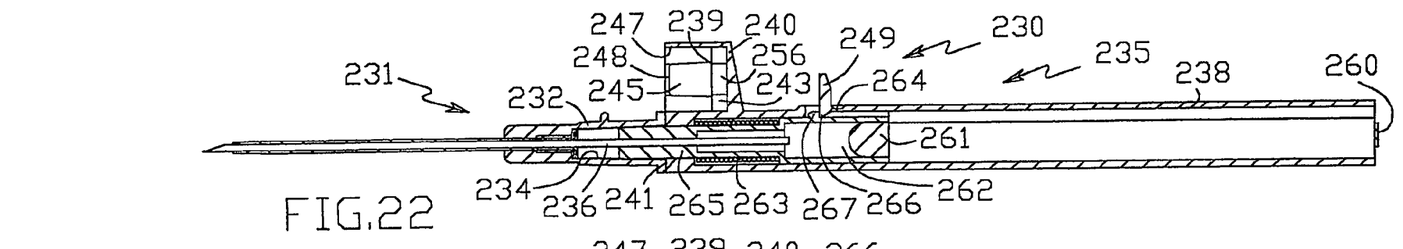
FIG. 22 shows the longitudinal section of the catheter introducer before the catheter emplacement.
Figure 23:
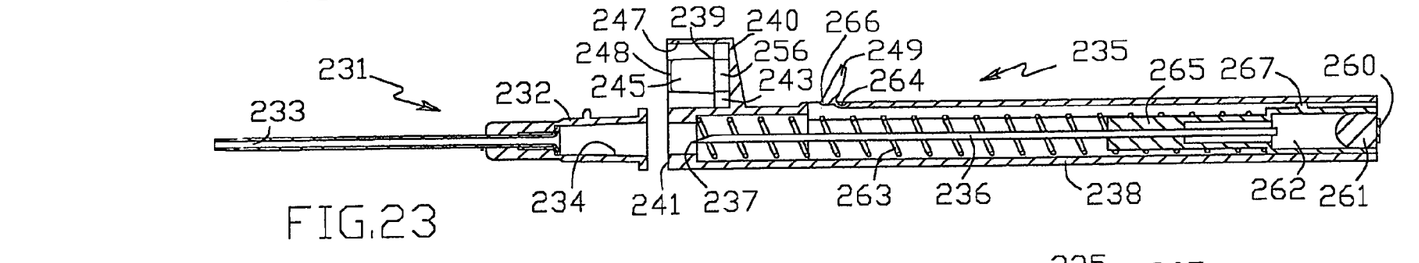
FIG. 23 shows the longitudinal section of the catheter introducer after the catheter emplacement and the needle retraction into the protection position.
Figures 24, 25:
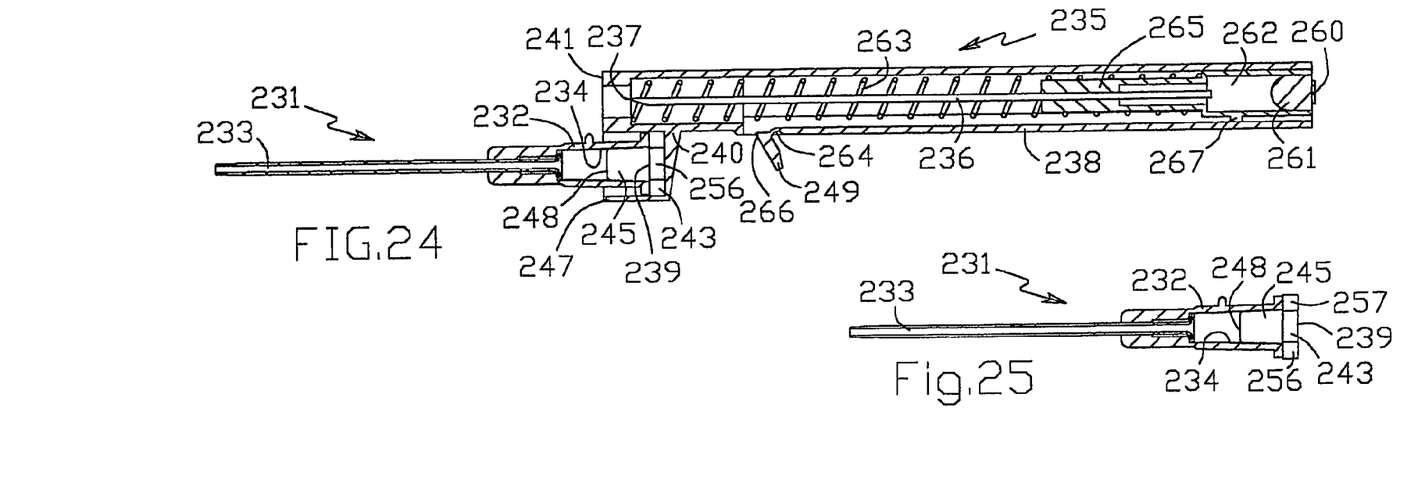
FIG. 24 shows the longitudinal section of the catheter introducer in the stage of the catheter cap mounting onto the catheter.
FIG. 25 shows the longitudinal section of the catheter closed with the catheter cap.
Figure 26:
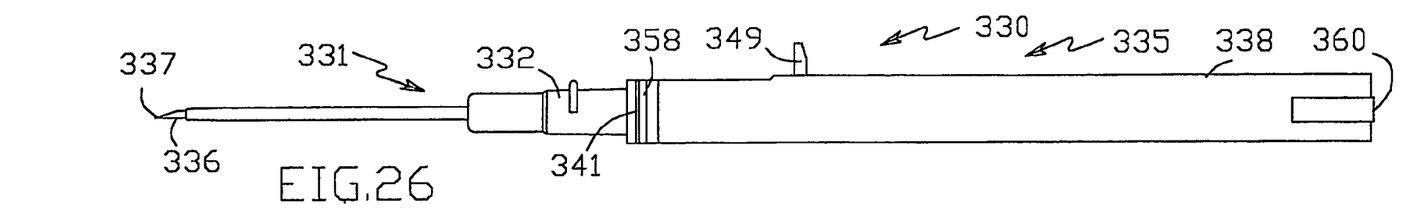
FIG. 26 shows the general side view of the catheter introducer before the catheter emplacement.
Figure 27:
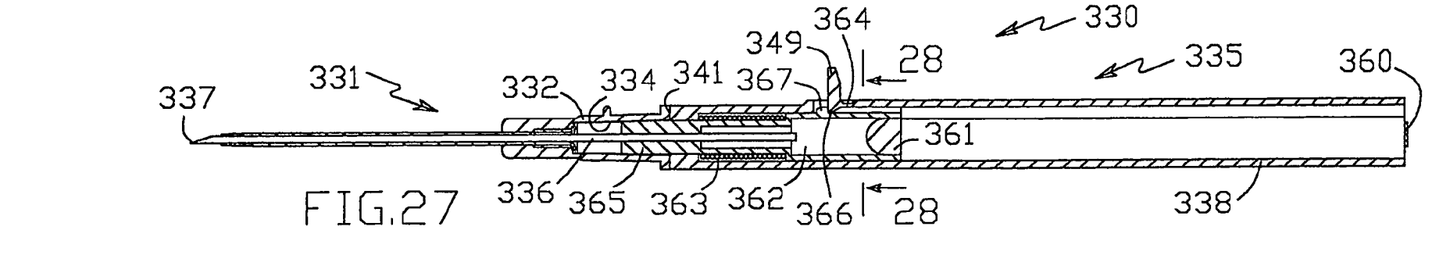
FIG. 27 shows the longitudinal section of the catheter introducer before the catheter emplacement.
Figures 28, 29:
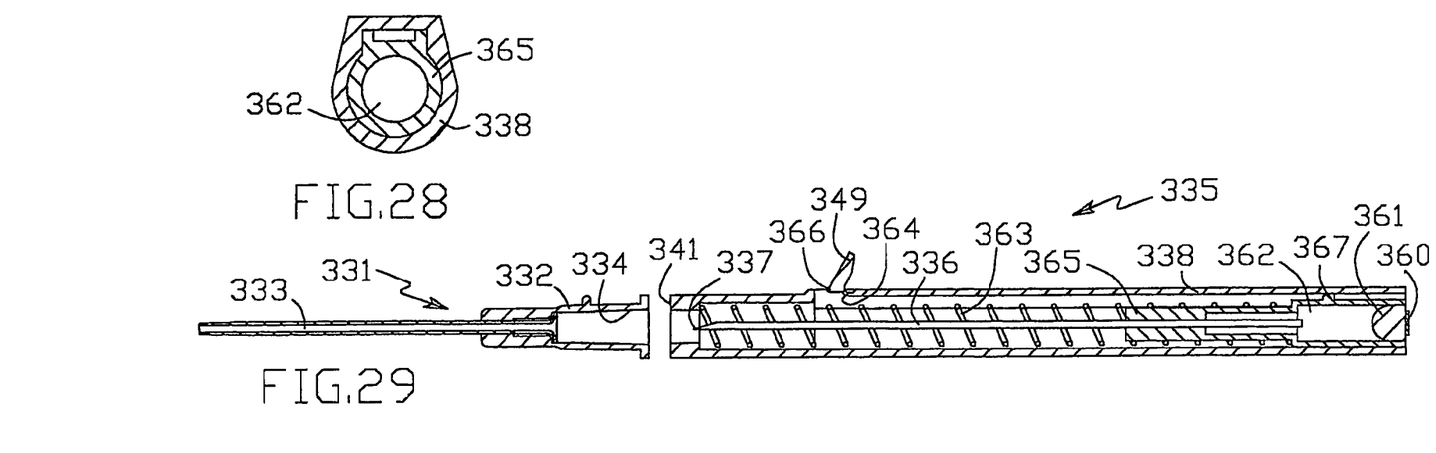
FIG. 28 shows the cross section of the catheter introducer before the catheter emplacement, made in the zone of the flash chamber location.
FIG. 29 shows the longitudinal section of the catheter introducer after the catheter emplacement and the needle retraction into the protection position.
Figure 30:
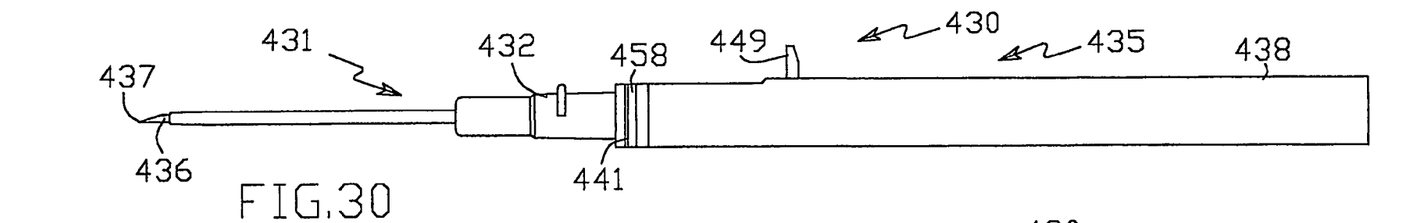
FIG. 30 shows the general side view of the catheter introducer before the catheter emplacement.
Figure 31:
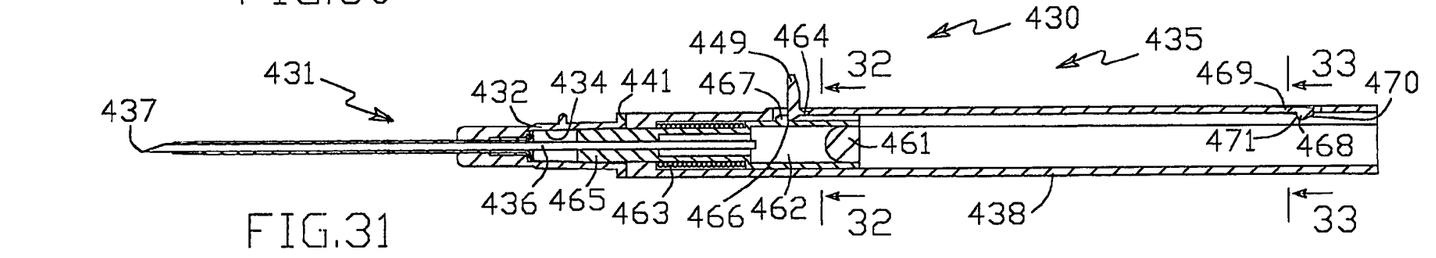
FIG. 31 shows the longitudinal section of the catheter introducer before the catheter emplacement.
Figures 32, 33, 34:
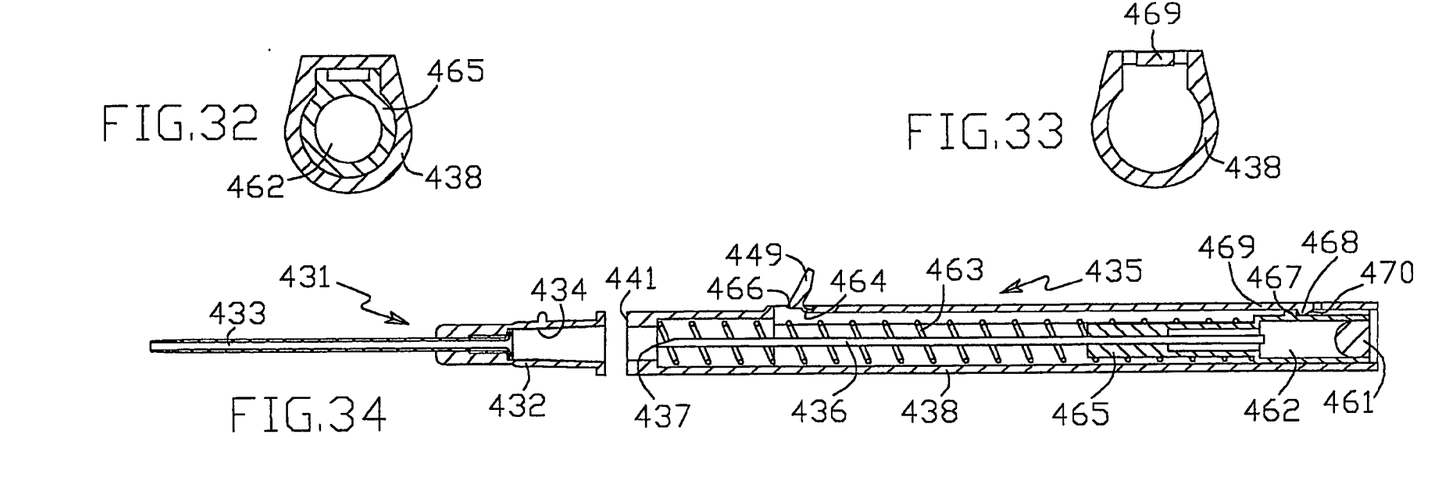
FIG. 32 shows the cross section of the catheter introducer before the catheter emplacement, made in the zone of the flash chamber location.
FIG. 33 shows the cross section of the catheter introducer before the catheter emplacement, made in the zone of the impact damper location.
FIG. 34 shows the longitudinal section of the catheter introducer after the catheter emplacement and the needle retraction into the protection position.
Figure 35:
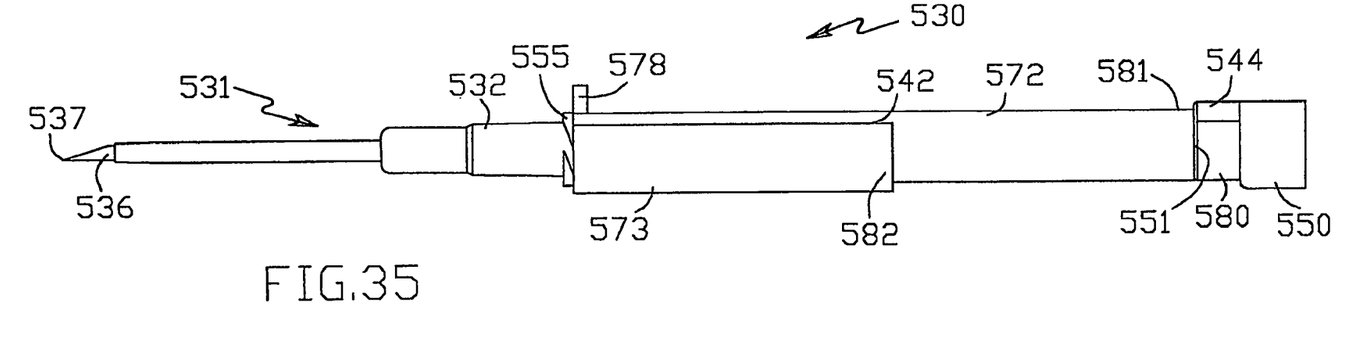
FIG. 35 shows the general side view of the catheter introducer in the duty ready position.
Figures 36, 37:
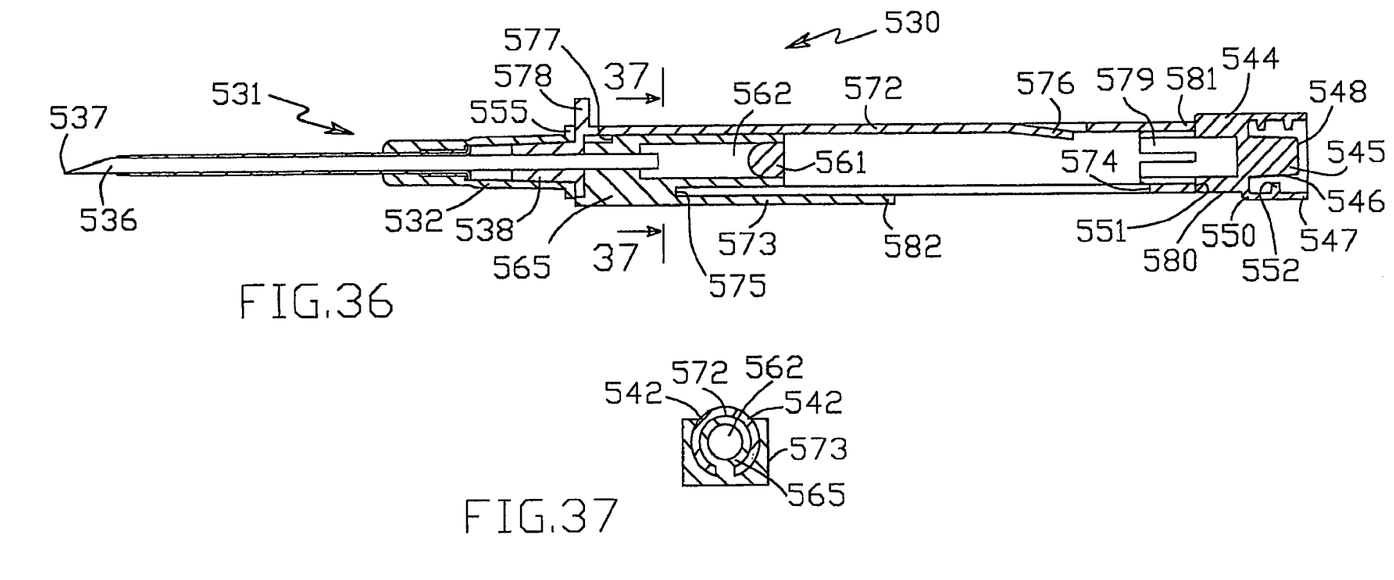
FIG. 36 shows the longitudinal section of the catheter introducer in the duty ready position.
FIG. 37 shows the cross section of the catheter introducer in the duty ready position.
Figure 38:
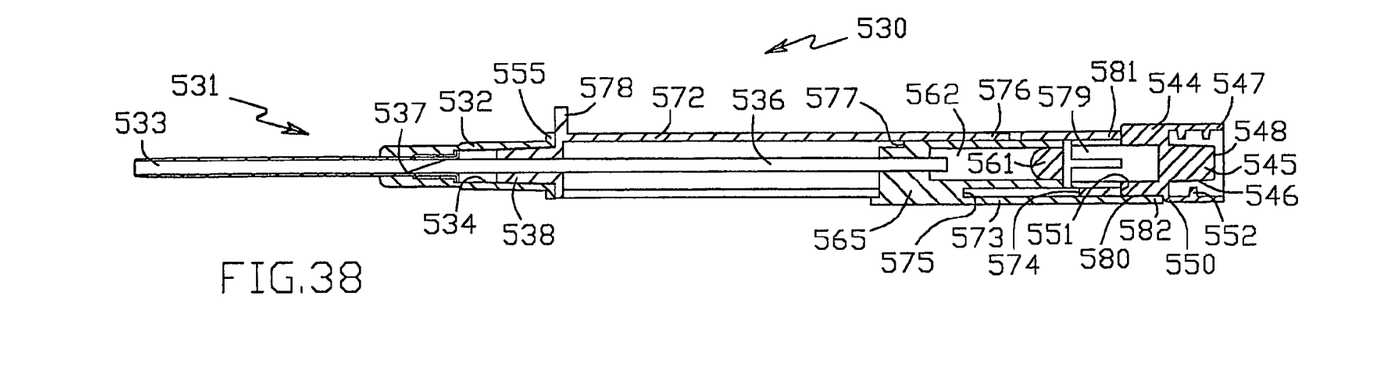
FIG. 38 shows the longitudinal cross section of the catheter introducer at the moment of the catheter cap transposition from the needle hub guide to the needle hub.

In another version embodiment, catheter introducer 230 (FIGS. 19 to 25) includes catheter 231 having catheter hub 232 and through axial channel 233 with a proximal end portion made as female luer lock portion 234. It also includes needle assembly 235 having a needle unit, which comprises needle 236 with distal sharp point 237 extending through catheter axial channel 233 and needle hub 265 with flash chamber 262 closed with liquid tight but air permeable plug 261. The safety means of catheter introducer 230 includes protector 238 in the form of a barrel for protecting needle distal sharp point 237 after introducing catheter 231 into a blood vessel. Barrel 238 contains needle 236 in the needle protection position (FIGS. 23, 24) and is provided with a stop means in the form of flexible ribbon 260. The latter is located at the proximal end of barrel 238 and designed for restricting the proximally directed displacement of needle 236 during its retracting into the protection position. Flexible ribbon 260 also fulfils the role of an impact damper cushioning the impact of plug 261 and the stop means at the end of the needle retraction into the protection position. The presence of the impact damper improves the ergonomic properties of the catheter introducer, therewith the performance of the impact damper and stop means as a single part allows avoiding the increase of the catheter introducer cost. In version embodiment, flexible ribbon is made in the form of an adhesive cellotape stuck to barrel 238. The safety means also includes springy retracting element 263 made as a spiral compression spring, trigger 249 connected to barrel 238 through thin flexible link 264, and latch 266. Barrel 238, trigger 249 and latch 266 are made as a single part, therewith flexible link 264 provides the mobility of trigger-latch 249, 266 relative to barrel 238. This decreases the cost of the fabrication of catheter introducer 230. Latch 266 protrudes inside barrel 238 and has the sloping proximal surface, which along with flexible link 264 simplifies assembling the barrel and a needle unit. In the duty ready position (FIG. 22), spring 263 is retained in compressed state due to abutting ridge 267 of needle hub 265 against latch 266. After emplacing catheter 231, operator pulls trigger 249 in proximal direction thereby lifting latch 266 and releasing spring 263, which retracts the needle unit into the retraction position. In doing so, operator deforms flexible link 264 so that it becomes unfit for repeated use. The mode of using trigger 249, specifically the need of pulling it in the proximal direction, allows the arrangement of the trigger somewhat proximally of the disposition of operator's fingers, abutting against ribs 258, 259. This improves the operation convenience and increases the operation reliability, hampering inadvertent the trigger actuation and the needle unit premature retraction. The proximally directed movement needed for the trigger actuation is not inherent in operator's natural motions. This additionally heightens the reliability of the catheter introducer operation, hampering the inadvertent trigger actuation. Moreover, more simple and cheaper soft shipping package of the catheter introducer may be used, since the trigger cannot be actuated by simple external press. In turn, the soft shipping package obviates the restriction for using the catheter introducer with the catheters having a side port and side wings. As a result, the scope of catheter introducer application widens.

Catheter introducer 230 is provided with catheter cap 239, which is positioned on the top of protector 238 of needle assembly 235 at protector distal end 241 and its tapered male luer member 245 is directed distally. Catheter cap 239 is housed inside receptacle 240 and has back 243 with two lateral projections 256, 257, which enter lateral slots 242 in receptacle 240. Projections 256, 257 and slots 242 create the stabilizing means preventing catheter cap 239 from rotation relative to needle assembly 235 during mounting catheter cap 239 onto catheter 231. Otherwise, the design, properties, operation and advantages of catheter cap 239 are identical to catheter cap 39 shown in FIGS. 1 to 12.

In another version embodiment, catheter introducer 330 (FIGS. 26 to 29) is made without the catheter cap and its mounting means. Otherwise, catheter introducer 330 is no different from catheter introducer 220, shown in FIGS. 19 to 25, including their designs, operations and advantages, and their identical elements have the same two last numerals of the designations. It means, that catheter introducer 330 can be applied independently of the catheter cap and provide substantial advantages connected with its trigger, latch and damper.

In another version embodiment, catheter introducer 430 (FIGS. 30 to 34) also is made without the catheter cap and its mounting means. However, as distinct from the version shown in FIGS. 26 to 29, its impact damper is made as a friction member 469 in the form of a resilient leg declined downward at a small angle to the axis of barrel 438. During movement into the protection position, needle hub 465 first comes into contact with resilient leg 469, which takes up the movement energy of needle hub 465 as a result of the friction between them. This substantially weakens the impact between ridge 467 of needle hub 465 and the stop means made in the form of a protrusion 468 of resilient leg 469. Therewith, the stopping process includes the action of resilient leg 469 at first stage and the impact with protrusion 468 at finish stage. Thus, resilient leg 469 partly also relates to the stop means. Protrusion 468 has proximal sloping surface 470, which allows easy introduction of needle hub 465 into barrel 438 during their putting together. Distal surface 471 of protrusion 468 is disposed at small angle to vertical, allowing the withdrawal of inner mould core during introducer fabrication, but eliminating the movement of needle hub 465 proximally beyond barrel 438 during introducer operation. Resilient leg 469, protrusion 468 and barrel 438 are made as a single part. The additional advantages of catheter introducer 430 are the design simplicity and minimized detail number. Otherwise, catheter introducer 430 is no different from catheter introducer 220, shown in FIGS. 19 to 25, including their designs, operations and advantages, and their identical elements have the same two last numerals of the designations.

In another version embodiment (not shown), a catheter cap is detachably positioned at the middle part of the needle assembly and the tapered male luer member of the catheter cap is directed laterally and outwardly.

In another version embodiment (not shown), a catheter cap is detachably retained in the receptacle on the needle assembly only by friction forces without special stabilizing means preventing the rotation of the catheter cap relative to the needle assembly. This allows using practically all known catheter cap designs with the present catheter introducer, substantially-widening its application scope and reducing its cost.

In another version embodiment (not shown), the stabilizing means preventing the rotation of the catheter cap relative to the needle assembly is made in the form of a thread on the lateral surface of the catheter cap and the interior of the catheter cap receptacle.

In another version embodiment (not shown), the stabilizing means preventing the rotation of the catheter cap relative to the needle assembly is made in the form of interacting a female conical portion and a tapered male element one of which is disposed on the catheter cap and the other in the catheter cap receptacle.

In another version embodiment (not shown), the catheter cap and the detail of the needle assembly on which the catheter cap is positioned are made as a single part, so that the catheter cap is connected to the needle assembly with a fragile link to be easy broken after mounting the catheter cap onto the catheter.

Figures 39, 40:
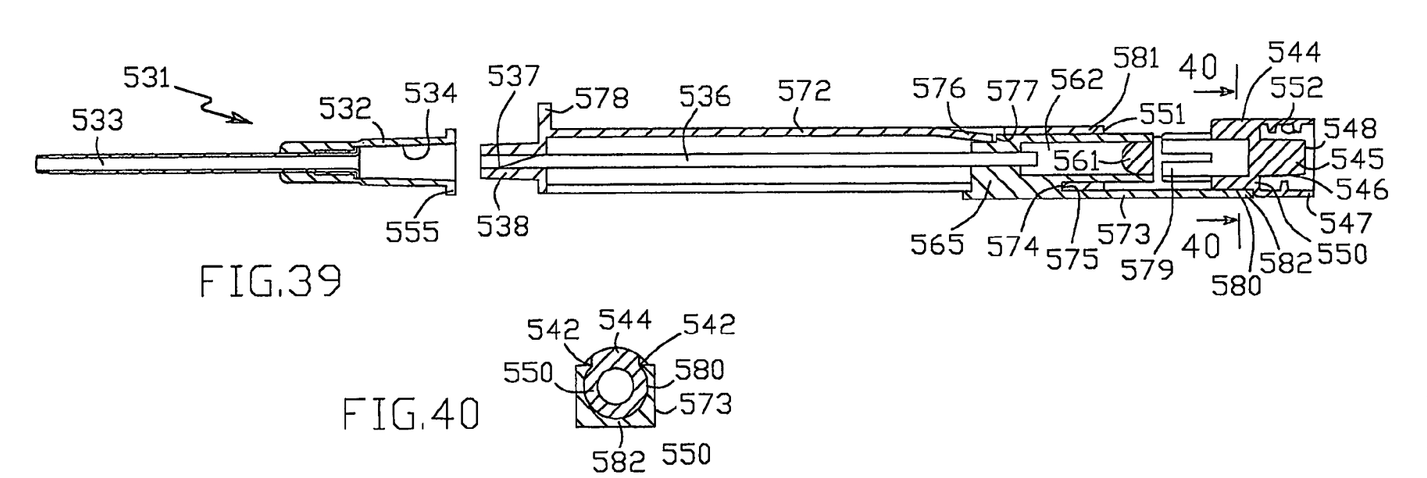
FIG. 39 shows the longitudinal section of the catheter introducer after the catheter emplacement, the needle retraction into the protection position and the catheter cap transposition from the needle hub guide to the needle hub.
FIG. 40 shows the cross section of the catheter introducer in the needle protected position.

In another version embodiment, catheter introducer 530, shown in FIGS. 35 to 40, has the safety means providing the needle retraction into the protected position by means of the manual drive. To retract needle 536 into its protected position (FIG. 39), operator holds gripping member 573 by hand and displaces needle hub 565 including flash chamber 562 proximally relative to needle hub guide 572, repelling from rib 578. At the end of this displacement, flexible fixing element 576 of guide 572 is butted up against fixing ledge 577 of needle hub 565 preventing needle hub 565 from displacing distally relative to guide 572. At the same time, edge 575 of needle hub 565 is butted up against edge 574 of guide 572 preventing needle hub 565 from displacing proximally relative to guide 572. Thus, needle hub 565 is fixed in the needle protected position. In duty ready position (FIGS. 35, 36), proximal end 582 of gripping member 573 made as a single part with needle hub 565 is located distally of proximal end 581 of guide 572, and catheter cap 550 is detachably mounted at guide proximal end 581 by slit shank 579 of catheter cap 550. During the transition of needle hub 565 from the duty ready position into the needle protected position (FIG. 38), catheter cap 550 is disengaged from guide proximal end 581 and engaged with needle hub proximal end 582. As a result, needle hub proximal end 582 is located proximally of guide proximal end 581, and catheter cap 550 is detachably engaged with needle hub proximal end 582 by means of the friction forces between outer surface 580 of catheter cap 550 and the interior of needle hub proximal end 582 (FIG. 39). In this position, catheter cap 550 is used for closing catheter 531 identical to its using in the above described catheter introducer 130 (FIGS. 13 to 18). Otherwise, catheter introducer 530 has the details identical to the above versions and having the same two last numerals of their designation. Catheter introducer 530 allows additional widening the application scope of the catheter introducers with the catheter cap and provides the advantages identical to that for the previous versions.

The invention claimed is:

1. A catheter introducer, comprising:
a catheter having a catheter hub and an axial through channel with a proximal end portion made as a female luer lock portion;
a needle assembly including
a needle with a distal sharp point, which extends through said catheter channel, and
a safety means having a protector for protecting said needle distal sharp point after introducing said catheter into a blood vessel,
wherein said needle assembly is in a protected position when said needle is protected by said protector, wherein in said protected position said needle assembly has a distal end and a proximal end;
a catheter cap having a tapered male luer member with a tapered end for occluding a proximal opening of said catheter after the transposition of said needle to said protected position, said catheter cap being detachably mounted on said needle assembly; and
mounting means for detachable mounting of said catheter cap on said needle assembly,
wherein said mounting means includes stabilizing means that prevents rotation of said tapered male luer member with respect to said needle assembly when mounting said catheter cap onto said catheter, and
wherein when said needle assembly is in said protected position said catheter cap is positioned at either of said ends of said needle assembly, and said tapered end of said tapered male luer member is directed proximally when said catheter cap is positioned at said proximal end of said needle assembly and distally when said catheter cap is positioned at said distal end of said needle assembly.

2. The catheter introducer of claim 1, wherein said mounting means has first and second mounting elements one of which is disposed on said needle assembly and the other on said catheter cap, wherein said stabilizing means is made as at least one slot and at least one projection, one of which slot and projection is located on said first mounting element and the other of which slot and projection is located on said second mounting element wherein said projection slidably enters said slot.

3. The catheter introducer of claim 2, wherein said catheter cap is detachably retained on said needle assembly by friction between said first and second mounting elements.

4. The catheter introducer of claim 1 and further including shielding means preventing said tapered luer member from accidental contact with an operator, wherein said shielding means is made as a shielding wall enclosing said tapered male luer member and protruding beyond said tapered end.

5. The catheter introducer of claim 1, wherein said catheter cap is disposed on said protector.

6. The catheter introducer of claim 1, wherein said needle assembly includes a hub ,and wherein said catheter cap is disposed on said hub.

7. The catheter introducer of claim 4, wherein one of said mounting elements is disposed on said needle assembly and forms a receptacle in which said catheter cap is housed and wherein said receptacle acts as said shielding means.

8. The catheter introducer of claim 1, wherein said catheter cap is provided with a thread for fixing said catheter cap onto said catheter.

* * * * *